United States Patent [19]
Carlson

[11] 4,100,537
[45] Jul. 11, 1978

[54] MONITOR FOR GAS PIPING SYSTEM
[75] Inventor: Peter B. Carlson, Orange, Calif.
[73] Assignee: Taylor Medical Oxygen Services, Inc., Orange, Calif.
[21] Appl. No.: 822,927
[22] Filed: Aug. 8, 1977
[51] Int. Cl.$^2$ ............................................. G08B 21/00
[52] U.S. Cl. .................................... 340/626; 340/605; 340/327
[58] Field of Search ............... 340/240, 229, 242, 236, 340/372, 378, 241, 326, 327

[56] References Cited
U.S. PATENT DOCUMENTS

| | | | |
|---|---|---|---|
| 1,219,723 | 3/1917 | Gracey et al. | 340/229 |
| 1,855,321 | 4/1932 | Shackleton | 340/242 |
| 1,986,479 | 1/1935 | Lowe et al. | 340/240 X |
| 2,004,769 | 6/1935 | Shanklin | 340/242 |
| 2,129,261 | 9/1938 | Chase et al. | 340/240 X |
| 2,723,388 | 11/1955 | Jacobs | 340/236 |
| 2,735,081 | 2/1956 | Hosford | 340/DIG. 1 |
| 3,184,958 | 5/1965 | Eaton | 340/242 X |
| 3,336,584 | 8/1967 | Kaiser | 340/242 |
| 3,350,704 | 10/1967 | Kessler | 340/242 |

FOREIGN PATENT DOCUMENTS 923,812  4/1963  United Kingdom ............ 340/237 R

Primary Examiner—John W. Caldwell, Sr.
Assistant Examiner—Daniel Myer
Attorney, Agent, or Firm—Philip M. Hinderstein

[57] ABSTRACT

Apparatus for monitoring the pressure in a gas line and providing a visual and audible indication of a high or low pressure condition, the gas line having a pressure sensor for generating high and low pressure signals, comprising a visual indicator responsive to the high pressure signal for providing a high pressure visual indication, a visual indicator responsive to the low pressure signal for providing a low pressure visual indication, a system normal visual indicator which is normally maintained in an "on" condition, an audible alarm, circuit means responsive to either of the high or low pressure signals for turning off the system normal visual indicator and for activating the audible alarm, and a manual switch for deactivating the audible alarm.

5 Claims, 3 Drawing Figures

U.S. Patent     July 11, 1978     4,100,537
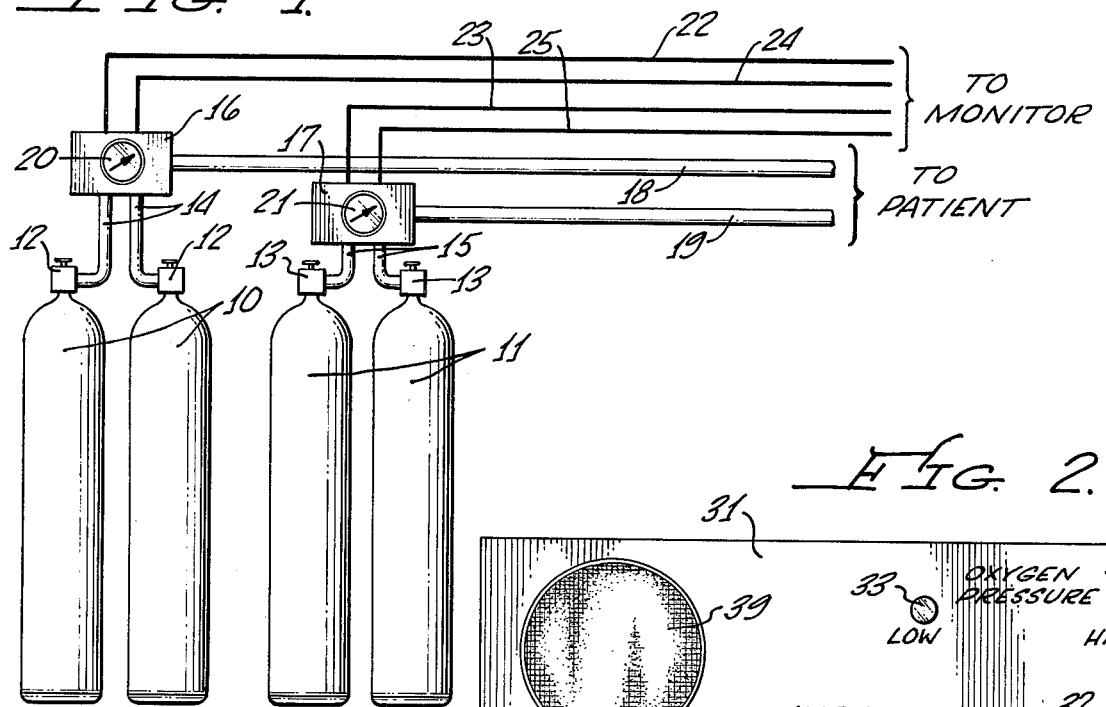
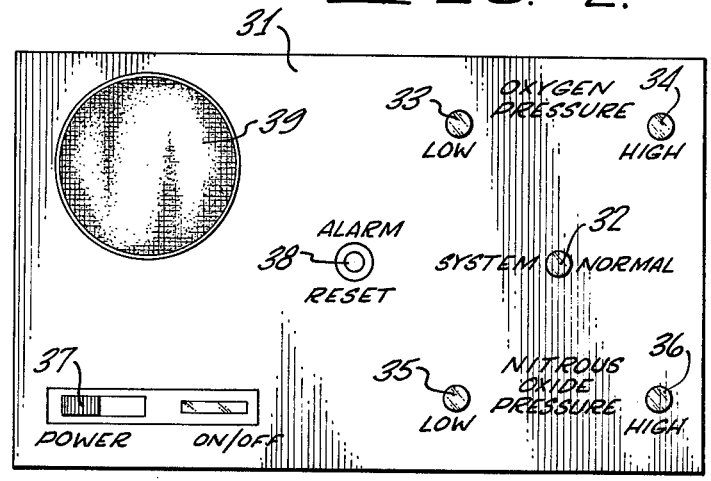
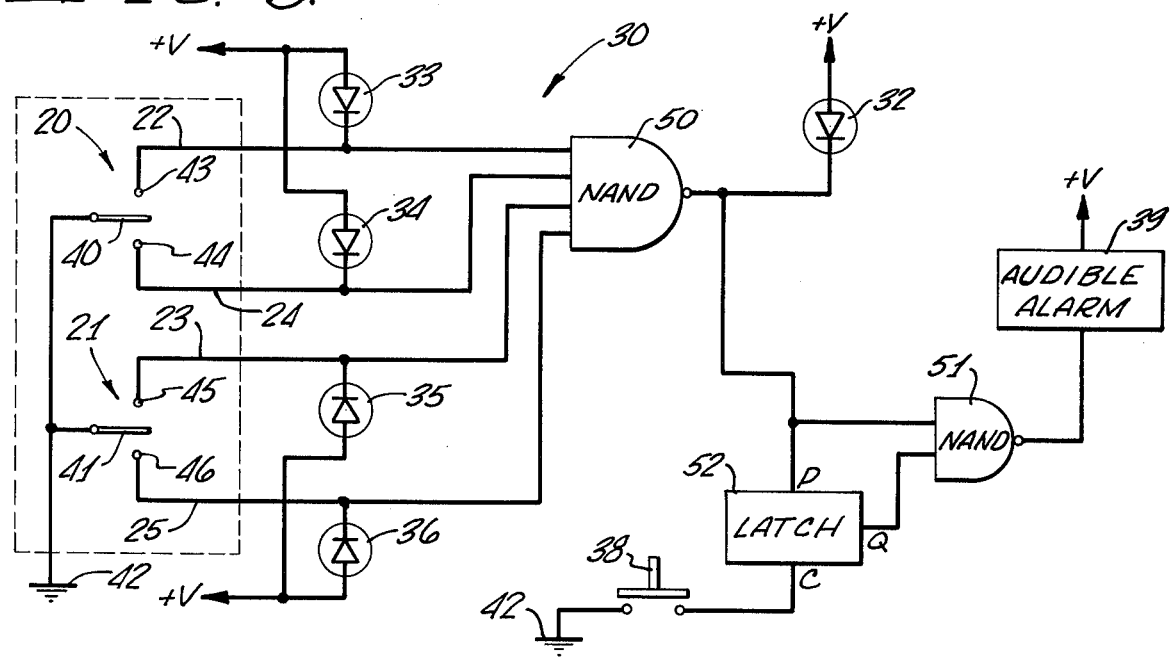

MONITOR FOR GAS PIPING SYSTEM

BACKGROUND OF THE INVENTION

1. Field of the invention.

The present invention relates to a monitor for gas piping systems and, more particularly, to a system designed to monitor nitrous oxide and oxygen pressure in medical gas piping systems.

2. Description of the Prior Art.

In virtually all doctor's and dentist's offices, and in other medical environments as well, there is usually provided one or more oxygen and nitrous oxide tanks which the doctor or dentist uses on a patient. The gas is conducted from the tanks to the patient via a gas piping system. Each such tank, or, in the case of multiple tanks, each such piping system, usually includes provision for a pressure gauge for monitoring the gas pressure. The pressure could become too high or too low because of a malfunction but, more commonly, the pressure decreases as the gas is used. The doctor requires notification of any of these conditions to insure a continous source of gas for the patient.

In most cases, the gas tanks and the pressure sensors are in a room separate from the room in which the doctor is treating the patient. Therefore, unless the doctor or nurse continuously checks the pressure gauges, there is no convenient way to determine what the status of the pressure gauges are.

In order to solve this problem, it has been suggested to provide a system for monitoring nitrous oxide and oxygen pressure in medical gas piping systems so that the doctor can be alerted to a high or low pressure situation without constant attention to the pressure sensors and gauges. While a number of systems have been developed for this purpose, none has been entirely satisfactory.

SUMMARY OF THE INVENTION

According to the present invention, there is provided a monitor for gas piping systems which solves all of the problems encountered heretofore. The present monitor includes an indicator panel including a visual indicator to indicate that the system is functioning normally. In the event of a high or low pressure condition in either the oxygen or the nitrous oxide system, the system normal visual indicator goes "off" and another visual indicator comes "on" indicating exactly what the probelm is, i.e. either high pressure or low pressure. At the same time, an audible alarm is activated to call the doctor's attention to the indicator panel. The audible alarm can be turned off by pushing a reset button, but the visual indicator which indicates the nature of the problem will remain lit as long as the system is on and until the problem is corrected.

Briefly, the present apparatus for monitoring the pressure in a gas line and providing a visual and audible indication of a high or low pressure condition, the gas line having a pressure sensor for generating high and low pressure signals, comprises a visual indicator responsive to the high pressure signal for providing a high pressure visual indication, a visual indicator responsive to the low pressure signal for providing a low pressure visual indication, a system normal visual indicator which is normally maintained in an "on" condition, an audible alarm, circuit means responsive to either of the high or low pressure signals for turning off the system normal visual indicator and for activating the audible alarm, and a manual switch for deactivating the audible alarm.

OBJECTS

It is therefore an object of the present invention to provide a monitor for gas piping systems.

It is a further object of the present invention to provide a system for monitoring nitrous oxide and oxygen pressure in medical gas piping systems.

It is a still further object of the present invention to provide a monitor for gas piping systems which will provide both a high pressure and a low pressure visual indication.

It is another object of the present invention to provide a monitor for gas piping systems which will provide an audible alarm in the presence of either a low or high pressure condition.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like or corresponding parts in the several figures and wherein:

BRIEF DESCRIPTION OF THE DRAWINGS

FIG. 1 is a schematic view showing the arrangement of nitrous oxide and oxygen tanks in a tank room;

FIG. 2 is a plan view of the indicator panel of the present monitor; and

FIG. 3 is a circuit diagram of the present monitor for gas piping systems.

DESCRIPTION OF THE PREFERRED EMBODIMENT

Referring now to the drawings and, more particularly to FIG. 1 thereof, a typical tank room in the office of a doctor or dentist includes multiple oxygen tanks 10 and multiple nitrous oxide tanks 11. Each of tanks 10 in connected via a valve 12 and a length of piping 14 to a manifold 16. Similarly, tanks 11 are connected via valves 13 and piping 15 to a manifold 17. From manifolds 16 and 17, oxygen and nitrous oxide are conducted to a patient via piping 18 and 19, respectively. While tanks 10 and 11 are disclosed as containing oxygen and nitrous oxide, respectively, it will be obvious that the present system is applicable to tanks containing other gases or liquids.

Manifolds 16 and 17 have pressure sensors or gauges 20 and 21, respectively, associated therewith which indicate the pressure in whichever tank is being used. Typically, only one of valves 12 and 13 are turned on to provide the appropriate gas. When the supply of gas is exhausted, the valve is shut off, the other valve is turned on, and the empty tank is replaced.

Pressure gauges 20 and 21 typically have the capability of providing an output signal when a predetermined low or high pressure is reached. Accordingly, when the predetermined low or high pressure is sensed by gauge 20, an output signal is provided on a line 22 or line 24, respectively. Pressure gauge 21 has a similar capability and provides an output on a line 23 at a predetermined low pressure and an output on a line 25 at a predetermined high pressure.

Referring now to FIGs. 2 and 3, the present monitor, generally designated 30, includes an indicator panel 31 on which is positioned a number of visual and audible indictors including a green system normal light 32, a red low oxygen pressure light 33, a red high oxygen pressure light 34, a red low nitrous oxide pressure light 35, a red high nitrous oxide pressure light 36, an on/off switch 37, an alarm reset button 38, and an audible alarm 39. All of these elements are interconnected as shown in FIG. 3.

Pressure gauge 20 has a movable arm 40 and pressure gauge 21 has a movable arm 41, both of which may be connected to ground 42. In the case of a low oxygen pressure situation, arm 40 contacts a terminal 43 to connect line 22 to ground 42. A high oxygen pressure situation causes arm 40 to contact a terminal 44 to connect line 24 to ground 42. A similar operation occurs with arm 41 which is capable of contacting a terminal 45 in a low nitrous oxide pressure situation or a terminal 46 in a high nitrous oxide pressure situation to connect lines 23 or 25, respectively, to ground 42.

Lights 33-36 may be light emitting diodes (LED's) having first, ends connected to lines 22, 24, 23, and 25, respectively, the other ends of which are connected to a suitable source of D.C. voltage. It is therefore evident tht under normal operating conditions, where neither arm 40 nor arm 41 is connected to any of terminals 43-46, there is no return connection for the voltage through lights 33-36 and they normally remain "off".

All of lines 22-25 are connected to the input of a NAND gate 50, the output of which is connected to one end of system normal visual indicator 32 (an LED), the other end of which is connected to a suitable source of D.C. voltage. The characteristic of a NAND gate is that if all of its inputs are "high", the output will be "low" and if any one of the inputs is "low", the output will be "high". Therefore, during normal operation of sensors 20 and 21, all of the inputs to gate 50 will be "high" and the output will be "low". This "low" output will provide a conducting path for the voltage across LED 32 and LED 32 will normally be "on".

On the other hand, if either arm 40 or 41 comes into contact with any of terminals 43, 44, 45, or 46, one of the inputs to NAND gate 50 will go "low", causing the output to go "high", thereby extinguishing LED 32. Under these circumstances, one of lamps 33-36 will come "on" and LED 32 will go "off" and this condition will continue until the appropriate sensor returns to the normal range.

The output of NAND gate 50 is also applied to one input of a NAND gate 51 and to the preset input P of a latch circuit 52. The Q output of latch circuit 52 is connected to the other input of NAND gate 51. The output of gate 51 is connected to one input of audible alarm 39, the other input of which is connected to a suitable source of D.C. voltage. Reset switch 38 is connected between ground 42 and the clear input terminal C of latch circuit 52.

Under normal operating conditions, where the output of gate 50 is "low", the output of gate 51 will be "high" regardless of the state of latch 52. As a practical matter, the Q output of latch 52 will also be "low". Since both inputs to gate 51 are "low", the output is "high" and there is no voltage across alarm 39 and it remains deactivated.

As explained previously, when a low or high pressure situation occurs, the output of NAND gate 50 is caused to go "high" and a high input is applied to one input of NAND gate 51. Furthermore, the transition at input P of latch 52 causes the circuit to flip, providing a "high" output at its Q output terminal. Since both inputs to NAND gate 51 are now "high", the output therefore goes "low", activating audible alarm 39. This calls the attention of the doctor or nurse to the low or high pressure condition.

In order to deactivate alarm 39, the doctor or nurse pushes reset button 38, thereby connecting clear input terminal C of latch 52 to ground 42. This causes latch 52 to return to its normal state where the Q output is "low". Therefore, even though the input to NAND gate 51 from NAND gate 50 is "high", the other imput thereto is "low", causing the output thereof to go "high", removing the voltage from across audible alarm 39.

Summarizing, through the use of pressure sensor 20 and 21 in the tank room, system pressure is monitored and a signal is sent to main indicator panel 31 in the doctor's office. Indicator panel 31 lights a green light 32 when system pressure is in a normal condition. When the system pressure goes below or above the normal pressure range, the green normal light 32 goes "off" and a red light turns "on" indicating whether the system pressure is too high or too low and whether it is oxygen pressure or nitrous oxide pressure. At the same time that one of the low or high lights comes "on", audible alarm 39 is sounded to alert the doctor or his personnel that there is a problem with the system pressure. Audible alarm 39 can be turned "off" by pushing reset button 38 on indicator panel 31. The red low or high pressure light will remain lit as long as the system is on or until the problem is corrected. If the system is turned off and on again before the problem is corrected, the red low or high pressure light will come on and the alarm will sound again. When the system is returned to normal operating pressure, the red light will shut off and the green system normal light 32 will come on indicating normal operation.

While the invention has been described with respect to a preferred physical embodiment constructed in accordance therewith, it will be apparent to those skilled in the art that the various modifications and improvements may be made without departing from the scope and spirit of the invention. Accordingly, it is to be understood that the invention is not to be limited by the specific illustraative embodiment, but only by the scope of the appended claims.

I claim:

1. Apparatus for monitoring the pressure in a gas line and providing a visual and audible indication of a high or low pressure condition, said gas line having a pressure sensor for generating high and low pressure signals, comprising:

a high pressure visual indicator responsive to said high presure signal for providing a high pressure visual indication;

a low pressure visual indicator responsive to said low pressure signal for providing a low pressure visual indication;

a system normal visual indicator;

means for normally maintaining said system normal visual indicator in an "on" condition;

an audible alarm;

means responsive to either of said high or low pressure signals for turning "off" said system normal visual indicator and for activating said audible alarm; and manual means for deactivating said audible alarm.

2. Apparatus according to claim 1, wherein said system normal visual indicator remains "off" as long as said pressure sensor continues to generate either a high or low pressure signal.

3. Apparatus according to claim 1, wherein said pressure sensor has a movable arm connected to ground and first and second terminals, said arm contacting said first terminal in the presence of a high pressure condition and contacting said second terminal in the presence of a low pressure condition, and further comprising:
- a source of voltage, said high pressure visual indicator being connected between said source of voltage and said first terminal, said low pressure visual indicator being connected between said source of voltage and said second terminal.

4. Apparatus according to claim 3, futher comprising:
- a NAND gate, said first and second terminals of said pressure sensor being connected to the inputs of said NAND gate, said system normal visual indicator being connected between the output of said NAND gate and said source of voltage.

5. Apparatus according to claim 4, further comprising:
- a second NAND gate, the output of said first-mentioned NAND gate being connected to one input of said second NAND gate; and
- a latch circuit having a preset input terminal, a clear input terminal, and a normally "low" output terminal, the output of said first NAND gate being connected to said preset input terminal, said output terminal being connected to another input of said second NAND gate, said audible alarm being connected between the output of said second NAND gate and said source of voltage, said manual means for deactivating said audible alarm being connected to said clear input terminal of said latch circuit.

* * * * *